(12) United States Patent
Gaskill, III et al.

(10) Patent No.: US 6,723,088 B2
(45) Date of Patent: Apr. 20, 2004

(54) LAPAROSCOPIC PORTING

(75) Inventors: Harold V. Gaskill, III, San Antonio, TX (US); Harold V. Gaskill, IV, San Antonio, TX (US)

(73) Assignee: Board of Regents, The University of Texas, Austin, TX (US)

( * ) Notice: Subject to any disclaimer, the term of this patent is extended or adjusted under 35 U.S.C. 154(b) by 0 days.

(21) Appl. No.: 10/027,123

(22) Filed: Dec. 20, 2001

(65) Prior Publication Data
US 2003/0149443 A1 Aug. 7, 2003

(51) Int. Cl.⁷ .............................................. A61B 17/00
(52) U.S. Cl. .......................................................... 606/1
(58) Field of Search ................................. 604/513, 264, 604/539; 600/204, 206, 208; 606/108, 1

(56) References Cited

U.S. PATENT DOCUMENTS

| | | |
|---|---|---|
| 4,617,933 A | 10/1986 | Hasson |
| 4,985,033 A | 1/1991 | Boebel et al. |
| 5,256,149 A | 10/1993 | Banik et al. |
| 5,257,973 A * | 11/1993 | Villasuso ..................... 604/539 |
| 5,364,367 A | 11/1994 | Banks et al. |
| 5,375,588 A | 12/1994 | Yoon |
| 5,380,302 A | 1/1995 | Orth |
| 5,403,336 A | 4/1995 | Kieturakis et al. |
| 5,437,645 A | 8/1995 | Urban et al. |
| 5,490,843 A * | 2/1996 | Hildwein et al. ...... 604/164.03 |
| 5,514,133 A * | 5/1996 | Golub et al. ..................... 606/1 |
| 5,540,648 A | 7/1996 | Yoon |
| 5,607,396 A | 3/1997 | Yoon |
| 5,616,131 A | 4/1997 | Sauer et al. |
| 5,653,718 A | 8/1997 | Yoon |
| 5,672,168 A * | 9/1997 | de la Torre et al. ............. 606/1 |
| 5,683,378 A * | 11/1997 | Christy ........................... 606/1 |
| 5,716,369 A | 2/1998 | Riza |
| 5,741,281 A | 4/1998 | Martin |
| 5,743,884 A | 4/1998 | Hasson et al. |
| 5,849,005 A * | 12/1998 | Garrison et al. ................ 606/1 |
| 5,911,728 A | 6/1999 | Sepetka et al. |
| 6,004,326 A | 12/1999 | Castro et al. |
| 6,004,337 A | 12/1999 | Kieturakis et al. |
| 6,080,181 A | 6/2000 | Jensen et al. |
| 6,083,203 A | 7/2000 | Yoon |
| 6,086,603 A | 7/2000 | Termin et al. |
| 6,093,176 A | 7/2000 | Dennis |
| 6,197,002 B1 * | 3/2001 | Peterson ................. 604/164.01 |
| 6,206,922 B1 | 3/2001 | Zdeblick et al. |
| 6,245,072 B1 | 6/2001 | Zdeblick et al. |
| 6,264,604 B1 | 7/2001 | Kieturakis et al. |

OTHER PUBLICATIONS

Patiño, M.D., J.F. and Quintero, M.D., G.A., "Asymptomatic Cholelithiasis Revisited", *World J. Surg.*, 22:1119–1124, 1998.

Leggett et al., "Resolving gastroesophageal reflux with laparoscopic fundoplication", *Surg. Endosc.*, 12:142–147, 1998.

* cited by examiner

*Primary Examiner*—Beverly M. Flanagan
(74) *Attorney, Agent, or Firm*—Fish & Richardson P.C.

(57) ABSTRACT

A retaining collar for laparoscopic surgery includes a compressible and elastic body that has an inner periphery and an outer periphery where the inner periphery forms a conduit for receiving and securing a tubular device. The retaining collar also includes a rigid portion attached to the compressible and elastic body. The rigid portion has an inner periphery, an outer periphery and a cam lock where the inner periphery forms an aperture that aligns with the conduit and the cam lock receives and retains a suture.

11 Claims, 2 Drawing Sheets

LAPAROSCOPIC PORTING

This invention relates to laparoscopic surgery and in particular to laparoscopic porting.

BACKGROUND OF THE INVENTION

Laparoscopic surgical methods require that a portal of entry be created in an abdominal wall. This portal of entry is used to introduce an inert gas, such as carbon dioxide, into an abdominal cavity in a process called insufflation. By blowing-up the abdominal cavity like a balloon, a space is created inside the abdominal cavity that allows the surgeon to easily view and access the operative field. This portal of entry is also used for the sequential introduction and removal of surgical instruments such as video imaging devices, scissors, graspers, and devices for suctioning and irrigation of the abdominal cavity.

Methods of placing these portals are well known to surgeons. One method is to make an incision in the skin of the abdominal wall with a knife or other cutting instrument. This incision is carried down to a fascia or an inner fibrous layer of the abdomen. An opening is then created in the fascia large enough to accommodate a cannula or a port device. Surgical sutures are then placed in the edges of the opening of the fascia. The cannula or port device is then inserted through the incision in the skin, through the hole in the fascia, and into the abdominal cavity. The sutures are then wrapped or tied around the port device to retain it during the operation. The port device then acts as a conduit for surgical instruments as described above.

It is an important object of the invention to provide improved laparoscopic porting.

BRIEF SUMMARY OF THE INVENTION

In one aspect, the invention is a retaining collar for laparoscopic surgery. The retaining collar includes a compressible and elastic body that has an inner periphery and an outer periphery where the inner periphery forms a conduit for receiving and securing a tubular device. The retaining collar also includes a rigid portion attached to the compressible and elastic body. The rigid portion has an inner periphery, an outer periphery and a cam lock. The inner periphery forms an aperture, that aligns with the conduit. The cam lock receives and retains a suture.

The invention may have one or more of the following features. The outer surface of the compressible and elastic body has a slit for receiving the suture. The outer periphery of the rigid portion having a slot for receiving the suture. The compressible and elastic body is constructed from polyurethane. The compressible and elastic body forms a sealing bias during carbon dioxide insufflation. The tubular device is a surgical device used in an abdominal area. The collar is conically shaped. The collar is bullet shaped.

In another aspect, the invention is a method of performing laparoscopic surgery. The method includes inserting a tubular device through a collar where the collar includes a compressible and elastic body having an inner periphery and an outer periphery. The inner periphery forms a conduit for receiving and securing the tubular device. The collar also includes a rigid portion attached to the compressible and elastic body where the rigid portion has an inner periphery, an outer periphery, and a cam lock. The inner periphery forms an aperture that is aligned with the conduit. The method also includes pulling a suture through the cam lock and retaining the suture using the cam lock.

One or more of the following features may be included in the invention. The method includes pulling the suture through the slit formed on the outer surface of the compressible and elastic body and pulling the suture through a slot of the outer periphery of the rigid portion. The method includes stitching through a tissue. The method includes forming a sealing bias during insufflation. The method includes passing surgical instruments through the tubular device.

The retaining collar provides a seal between the retaining collar and the opening in the abdominal wall to prevent the escape of carbon dioxide gas during insufflation due to the shape and compressible nature of the compressible and elastic body. In addition, the conduit through the compressible and elastic body of the retaining collar secures the tubular device while allowing variation in the diameter of the port device as well as adjustments in depth and position of the device while also maintaining a seal. Finally, the cam lock allows for easy accessibility in suturing an incision.

Other features, objects and advantages will become apparent from the following detailed description when read in connection with the accompanying drawing in which:

DETAILED DESCRIPTION OF THE INVENTION

Figure 1:
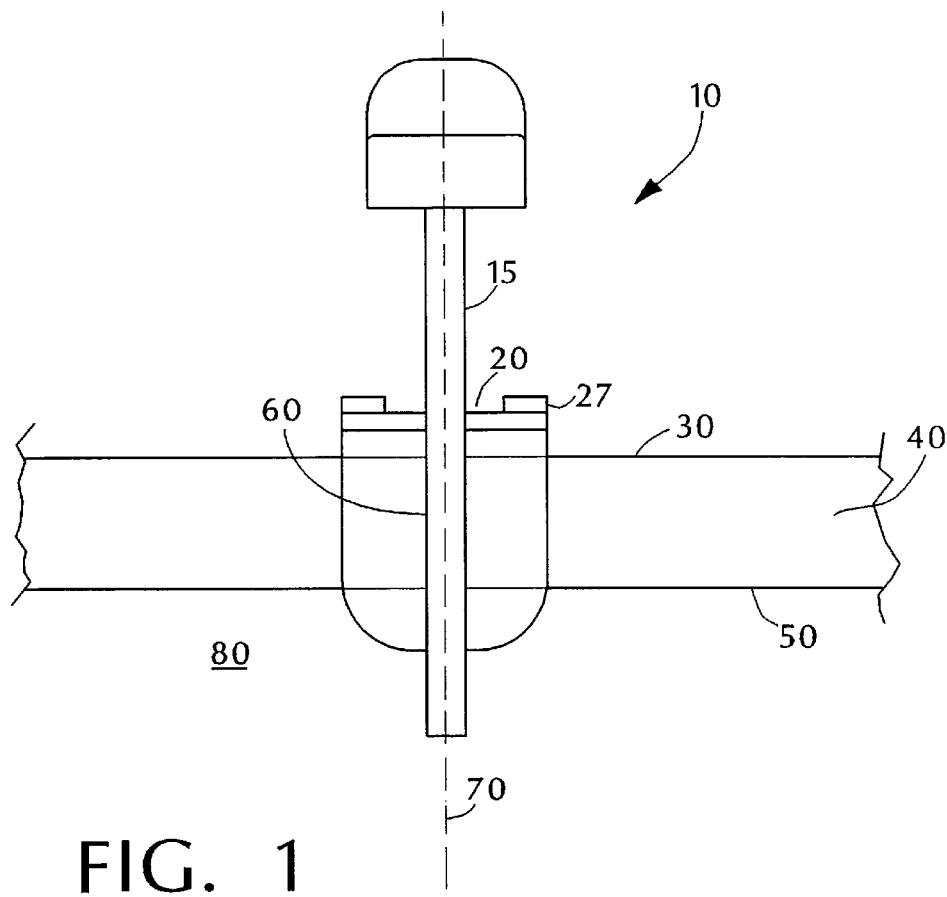
FIG. 1 is a cross-sectional view of a laparoscopic system with a retaining collar.
Figure 4:
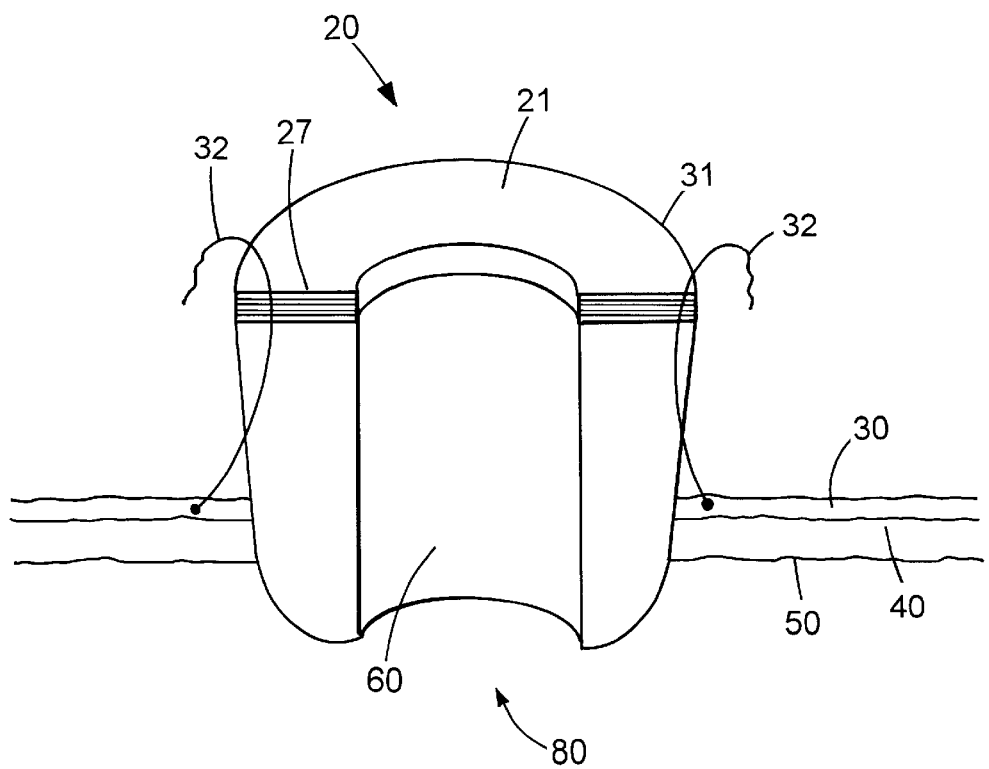
FIG. 4 is a side view of one-half of the retaining collar positioned in an abdomen.

Referring to FIG. 1, a laparoscopic system 10, used in a laparoscopic surgical procedure, includes a retaining collar 20 inserted into an incision. Retaining collar 20 extends through a skin tissue layer 30 and a subcutaneous tissue 40 down to a fascia tissue layer 50. A tubular device 15 is inserted through retaining collar 20 through a conduit 60. Conduit extends along a longitudinal axis 70. Tubular device 15 can be a trocar, a cannula, an obturator, or any tubular structure for surgical procedures performed in an abdominal area 80. As will be explained below, retaining collar 20 is constructed to act as a sealing bias against a loss of an inert gas (e.g., carbon dioxide) during insufflation while also securing tubular device 15. In addition, cam locks 27 of retaining collar 20 secure a suturing thread 32 (FIG. 4) used in suturing the incision.

Cam locks 27 and other cam-type locking devices incorporate two opposing curved surfaces held in opposition by a pivoting or flexing component. The opposing surfaces are characterized by a curved or spiral cross-section. The geometry of these devices produces a gripping action of increasing strength when tension is placed on a cord or suture placed between the opposing surfaces. The design of these cam locking devices is described in the literature pertaining to rope-retaining devices well-known to manufacturers of nautical equipment.

Figure 2:
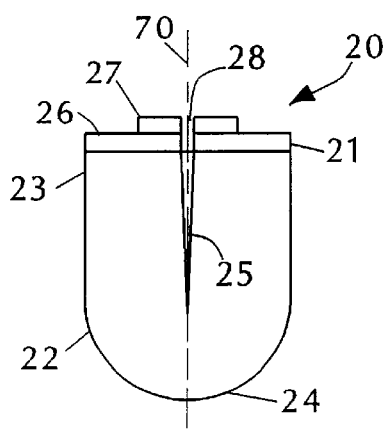
FIG. 2 is side view of a retaining collar for laparoscopic surgery.

Referring to FIGS. 1 and 2, retaining collar 20 includes a rigid top portion 21 and a flexible body 22. Flexible body 22 is bullet shaped so that after insertion into abdominal area 80, a wider end 23 of flexible body 22 is outside abdominal area 80, and a smaller end 24 of flexible body 22 is within subcutaneous tissue 40. The bullet shape accommodates and compensates for variations in the size of the opening into abdominal area 80. Flexible body 22 is made of a compressible material (e.g., compressible and elastic rubber, polyurethane, expanded latex, etc.). Flexible body 22 has slits 25 that begin extend from rigid portion 21 along longitudinal axis 70. In other embodiments, flexible body 22 is conically shaped.

Figure 3:
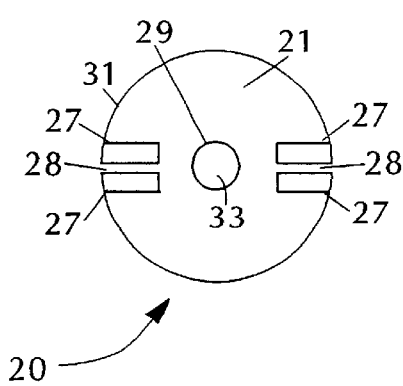
FIG. 3 is a top view of the retaining collar for laparoscopic surgery.

Referring to FIGS. 2 and 3, rigid top portion 21 has cam locks 27 positioned on a top surface 26 of the rigid top portion. Along a periphery 21 of rigid top portion 21 is a gap 28 that is aligned with a slit 25 of flexible body 22 along longitudinal axis 27. Rigid top portion 21 is made of plastic or other like rigid material capable of being sterilized for surgical procedures. An inner periphery 29 of rigid top portion 21 forms an aperture 33. Aperture 33 is aligned with conduit 60 forming a continuous passageway. Slit 25 can also be a groove.

During surgery, the surgeon makes the incision through skin 30 and subcutaneous tissue 40 to fascia 50. The diameter of the incision is smaller than the diameter of retaining collar 20. One or more retaining sutures 32 are then placed in the edges of the opening in the fascia 30. The surgeon inserts tubular device 15 through conduit 60. Conduit 60 has a diameter that is smaller than a diameter of tubular device 15. When tubular device 15 is inserted into retaining collar 20, conduit 60 expands to receive the tubular device.

When retaining collar 20 is inserted into the incision, the retaining collar is compressed circumferentially by the surrounding tissue and longitudinally by the retaining sutures as a natural consequence of securing the collar within the incision. The bullet shape and the compressible material of body 22 provides a snug and secure fit with skin 30, subcutaneous tissue 40 and fascia 50 to form a sealing bias. The sealing bias prevents the release of the inert gas from abdominal area 80 during insufflation.

A suture thread 32 stitched through skin 30 is brought through slit 25, through gap 28 and through cam locks 27. The placement of suture thread 32 through slit 25 and gap 28 and between cam locks 27 is accomplished by a mere tugging of anchored suture threads 32 up through cam locks 27. Suture thread 32 can be released to remain secure between cam locks 27. Tubular device 15 is then held securely by retaining collar 20. In this embodiment, slits 25 extend far enough along longitudinal axis 70 so that the suture thread 32 may easily be inserted between gap 28 and cam locks 27 without obstruction.

After the surgical procedure is complete, the surgeon uses the retaining sutures placed through fascia 30 to close the incision. The sutures are tied and knotted in the usual fashion for closing surgical incisions.

Other embodiments not described here are also within the scope of the following claims.

What is claimed is:

1. A retaining collar for laparoscopic surgery, comprising:

a compressible and elastic body having an inner periphery and an outer periphery, the inner periphery forming a conduit for receiving and securing a tubular device; and a rigid portion attached to the compressible and elastic body, the rigid portion having an inner periphery, an outer periphery and a cam lock; the inner periphery forming an aperture, the aperture aligning with the conduit, the outer periphery having a slot for receiving a suture, the cam lock receiving and retaining the suture;

wherein the outer periphery of the compressible and elastic body has a slit for receiving the suture.

2. The collar of claim 1, wherein the outer periphery of the rigid portion has a slot for receiving the suture.

3. The collar of claim 1, wherein the compressible and elastic body is constructed from polyurethane.

4. The collar of claim 1, wherein the compressible and elastic body forms a sealing bias during carbon dioxide insufflation.

5. The collar of claim 1, wherein the tubular device is a surgical device used in an abdominal area.

6. The collar of claim 1, wherein the collar is conically shaped.

7. The collar of claim 1, wherein the collar is bullet shaped.

8. A method of performing laparoscopic surgery, comprising:

inserting a tubular device through a collar, the collar includes;
      a compressible and elastic body having an inner periphery and an outer periphery, the inner periphery forming a conduit for receiving and securing the tubular device; and
   a rigid portion attached to the compressible and elastic body, the rigid portion having an inner periphery, an outer periphery and a cam lock; the inner periphery forming an aperture, the aperture aligning with the conduit;

pulling a suture through the cam lock;

retaining the suture using the cam lock;

pulling the suture through a slit formed on the outer periphery of the compressible and elastic body; and pulling the suture through a slot of the outer periphery of the rigid portion.

9. The method of claim 8, further comprising stitching through tissue.

10. The method of claim 9, further comprising forming a sealing bias during insufflation.

11. The method of claim 8, further comprising passing surgical instruments through the tubular device.

* * * * *